(12) United States Patent
Fuse et al.

(10) Patent No.: US 8,705,699 B2
(45) Date of Patent: Apr. 22, 2014

(54) MOBILE X-RAY DEVICE

(75) Inventors: Miyuki Fuse, Tokyo (JP); Takashi Shimohira, Tokyo (JP); Satoshi Arakawa, Dusseldorf (DE); Tatsuo Iiyama, Kanagawa (JP); Kenji Takata, Kanagawa (JP); Jun Fukazawa, Kanagawa (JP)

(73) Assignees: Hitachi Medical Corporation, Tokyo (JP); Fujifilm Corporation, Tokyo (JP)

( * ) Notice: Subject to any disclaimer, the term of this patent is extended or adjusted under 35 U.S.C. 154(b) by 292 days.

(21) Appl. No.: 13/257,054

(22) PCT Filed: Apr. 8, 2010

(86) PCT No.: PCT/JP2010/056369
§ 371 (c)(1),
(2), (4) Date: Sep. 16, 2011

(87) PCT Pub. No.: WO2010/122906
PCT Pub. Date: Oct. 28, 2010

(65) Prior Publication Data
US 2012/0008748 A1 Jan. 12, 2012

(30) Foreign Application Priority Data
Apr. 22, 2009 (JP) .................................. 2009-103797

(51) Int. Cl.
*H05G 1/10* (2006.01)
(52) U.S. Cl.
USPC ........................................... 378/102; 378/91
(58) Field of Classification Search
USPC ........................................ 378/91, 102, 198
See application file for complete search history.

(56) References Cited

U.S. PATENT DOCUMENTS

| 2002/0149345 A1* | 10/2002 | Takano et al. ................. 320/137 |
| 2005/0001599 A1 | 1/2005 | Seo |
| 2008/0073568 A1 | 3/2008 | Yamazaki et al. |
| 2008/0123814 A1* | 5/2008 | Curtis et al. .................. 378/102 |

FOREIGN PATENT DOCUMENTS

| JP | 4-322097 | 11/1992 |
| JP | 2006-14177 | 1/2006 |
| JP | 2008-73121 | 4/2008 |
| JP | 2009-1538847 | 7/2009 |

OTHER PUBLICATIONS

Catalogue of Regius Model 110, searched on Internet on Mar. 18, 2009,<URL:http://konicaminola.jp/healthcare/products/cr/regius110/index.html>.
International Search Report and Written Opinion for PCT International Application No. PCT/JP2010/056369 mailed on May 18, 2010.

* cited by examiner

*Primary Examiner* — Hoon Song
(74) *Attorney, Agent, or Firm* — Brundidge & Stanger P.C.

(57) ABSTRACT

A mobile X-ray device 1 is provided with a main body 2 having an X-ray generating part 10 and an image reader 50 for reading X-ray image information from an imaging plate storing the X-ray image information, a running part 60 for running the main body 2, a battery 70 for storing direct current electrical energy to be supplied to the running part 60 and discharging a direct current at a rated voltage of the running part 60, and a direct current power source voltage conversion part 80 for transforming direct voltage of the battery 70 to a rated voltage of the image reader 50, wherein the rated voltage of the image reader 50 transformed by the direct current power source voltage conversion part 80 is applied to the image reader 50.

3 Claims, 4 Drawing Sheets

MOBILE X-RAY DEVICE

TECHNICAL FIELD

The present invention relates to a mobile X-ray device, especially miniaturization and weight saving of mobile X-ray device.

BACKGROUND ART

There have conventionally been image readers in which X-ray photography is performed by using an imaging plate formed by applying a photostimulable phosphor on a support, X-ray absorption distribution of a subject accumulated in the imaging plate as a latent image is read out as X-ray image information, and the read-out image data are erased. For example, Non-patent document 1 discloses an image reader to be set up on a predetermined site and used. This image reader is connected to an electric socket provided on a wall surface of an X-ray room or the like, and driven with an alternating current.

PRIOR ART REFERENCE

Non-Patent Document

Non-patent document 1: Catalogue of REGIUS MODEL 110, searched on the Internet on Mar. 18, 2009<URL: http://www.konicaminolta.jp/healthcare/products/cr/regius110/index.html>

SUMMARY OF THE INVENTION

Object to be Achieved by the Invention

Since the image reader of Non-patent document 1 mentioned above is set up on a predetermined site such as an X-ray room and used, it cannot be used for confirming X-ray images on the spot during doctor's round in hospital. Therefore, there are mobile X-ray devices for doctor's round comprising an X-ray device carried on a mobile cart.

In view of usability in connection of moving, miniaturization and weight saving of mobile X-ray devices for doctor's round are desirable. However, there has been a problem that sufficient miniaturization and weight saving cannot be attained only by mounting an image reader on a mobile cart. In addition, there has also been a problem that, since mobile X-ray devices for doctor's round are moved every place in a hospital and used, and an electric power supply cannot always be secured on a site to which the devices are moved, they are required to afford longer movable time and longer operable time with preventing dead of battery.

The present invention was accomplished in light of the aforementioned problems, and aims at providing a mobile X-ray device that can be made smaller and lighter, and can also attain improvement of power efficiency.

Means for Achieving The Object

In order to achieve the aforementioned object, the mobile X-ray device of the present invention comprises a main body having an X-ray generating part and an image reader for reading X-ray image information from an imaging plate storing the X-ray image information, a running part for running the main body, a battery for storing direct current electrical energy to be supplied to the running part and discharging a direct current at a rated voltage of the running part, and a direct current power source voltage conversion part for transforming direct voltage of the battery to a rated voltage of the image reader, and is characterized in that the rated voltage of the image reader transformed by the direct current power source voltage conversion part is applied to the image reader.

Effect of the Invention

According to the present invention, the image reader can be driven by a direct current power supply with the direct current of the battery. Therefore, comparing with the conventional case where a mobile X-ray device is constituted by mounting an image reader driven by an alternating current power supply on a mobile cart, and a direct current of a battery is converted into an alternating current and used for driving the image reader by an alternating current power supply, an inverter required for conversion into alternating current can be eliminated, and miniaturization and weight saving of a mobile X-ray device can be thereby attained. Furthermore, it becomes unnecessary to convert the direct current of the battery into an alternating current, and therefore power efficiency can also be improved.

MODES FOR CARRYING OUT THE INVENTION

Hereafter, embodiments of the present invention will be explained. In all of the drawings for explaining the embodiments of the present invention, elements having the same function are indicated with the same numerals or symbols, and repetition of the explanations thereof are omitted in the following explanations.

Figure 1:
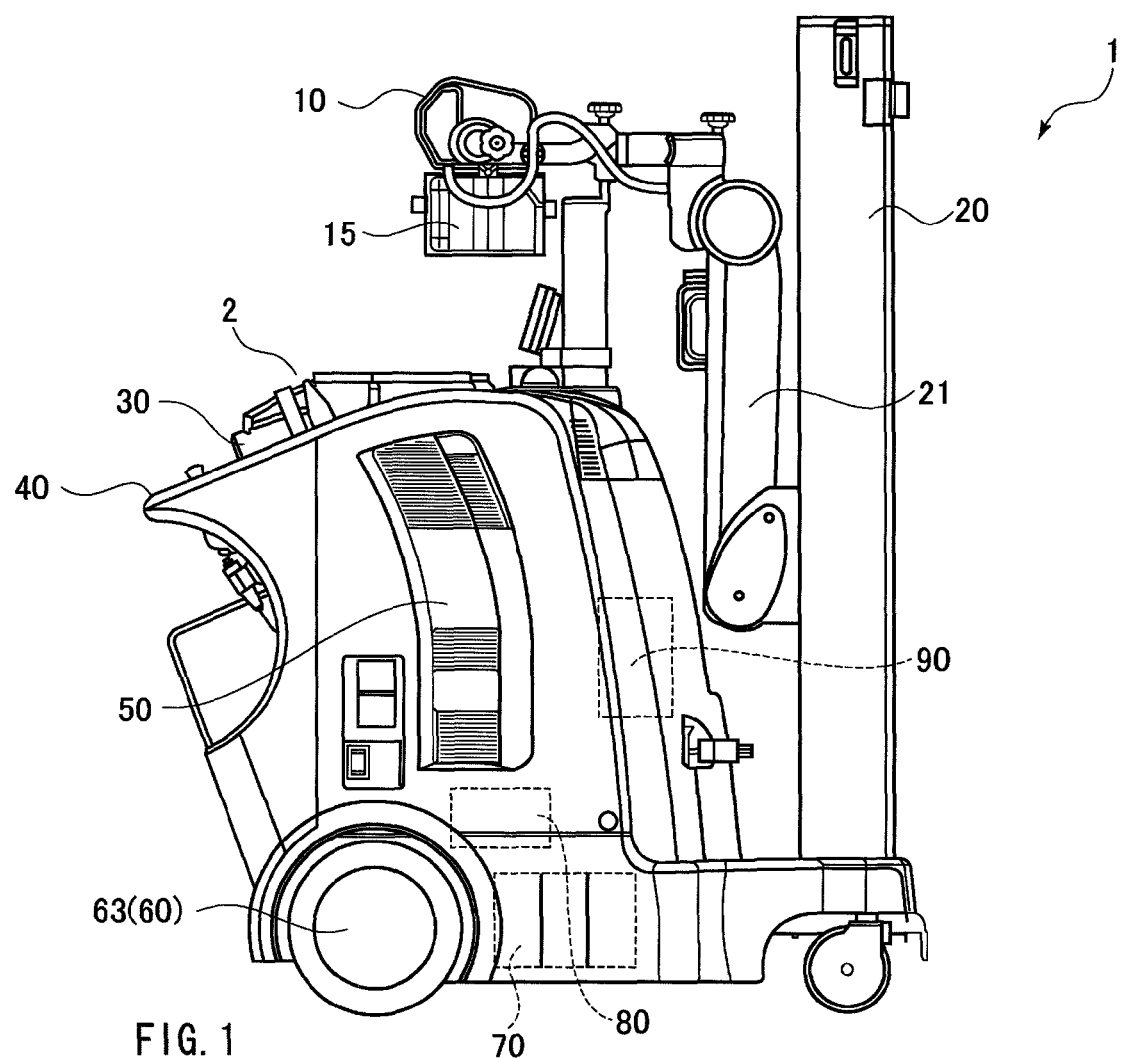
FIG. 1 shows an external view of the mobile X-ray device according to the first embodiment.

Hereafter, with reference to FIG. 1, schematic configuration of a mobile X-ray device 1 according to an embodiment of the present invention will be explained. FIG. 1 shows an external view of a mobile X-ray device according to the first embodiment.

The mobile X-ray device 1 according to this embodiment is provided with, as the major parts, a main body 2, a post 20 vertically disposed in front of the main body 2, a running part 60 provided under the main body 2 and the post 20, for running with carrying the main body 2 and the post 20.

An arm part 21 constituted by a pantograph arm is connected to the post 20. The arm part 21 may be constituted by a telescopic arm, instead of the pantograph arm. On the free end side of the arm part 21, an X-ray generating part 10 for generating X-ray and a collimator 15 for restricting irradiation area of X-ray are provided. By expanding or contracting, or rotating the arm part 21, the positions of the X-ray generating part 10 and the collimator 15 are moved so that X-ray is irradiated on an imaging part of a subject not shown in the drawing. Further, the collimator 15 defines irradiation area of X-ray so that X-ray is irradiated on an imaging part of the subject. An imaging plate not shown in the drawing is disposed at such a position that it should face the X-ray generating part 10 with the subject between them. A part of the X-ray generated by the X-ray generating part 10, the part passing through the subject, enters into the imaging plate. The X-ray that entered is converted into X-ray image information. As a result, X-ray absorption distribution of the subject is stored in the imaging plate as a latent image.

The main body 2 is provided with, on the side opposite to the post 20 (around the rear upper surface), a control panel 30 provided with various control keys and a display panel for displaying an X-ray image, and a handle 40 for driving to be grasped by an operator when the operator runs the mobile X-ray device 1. The handle 40 for driving has a brake for the mobile X-ray device 1, although not shown in the drawing, and it is configured so that the operator can brake the mobile X-ray device 1 with the hand grasping the handle 40 for driving.

The main body 2 is provided with, around the center, an image reader 50 for reading out the X-ray absorption distribution of the subject accumulated in the imaging plate as a latent image as image information, and erasing the read-out image data (henceforth referred to as "CR reader", CR is an abbreviation of computed radiography).

Under the main body 2, there are provided a running part 60 comprising a wheel 63, which is rotated by motor drive or manually, and a rechargeable battery 70 for storing direct current electrical energy to be supplied to the running part 60 and discharging a direct current at a rated voltage of the running part 60. Furthermore, in the inside of the main body 2, there are provided a direct current power source voltage conversion part (DC/DC converter) 80 for transforming voltage of the direct current supplied from the battery 70 to a rated voltage of the CR reader 50, and a control part 90.

Figure 2:
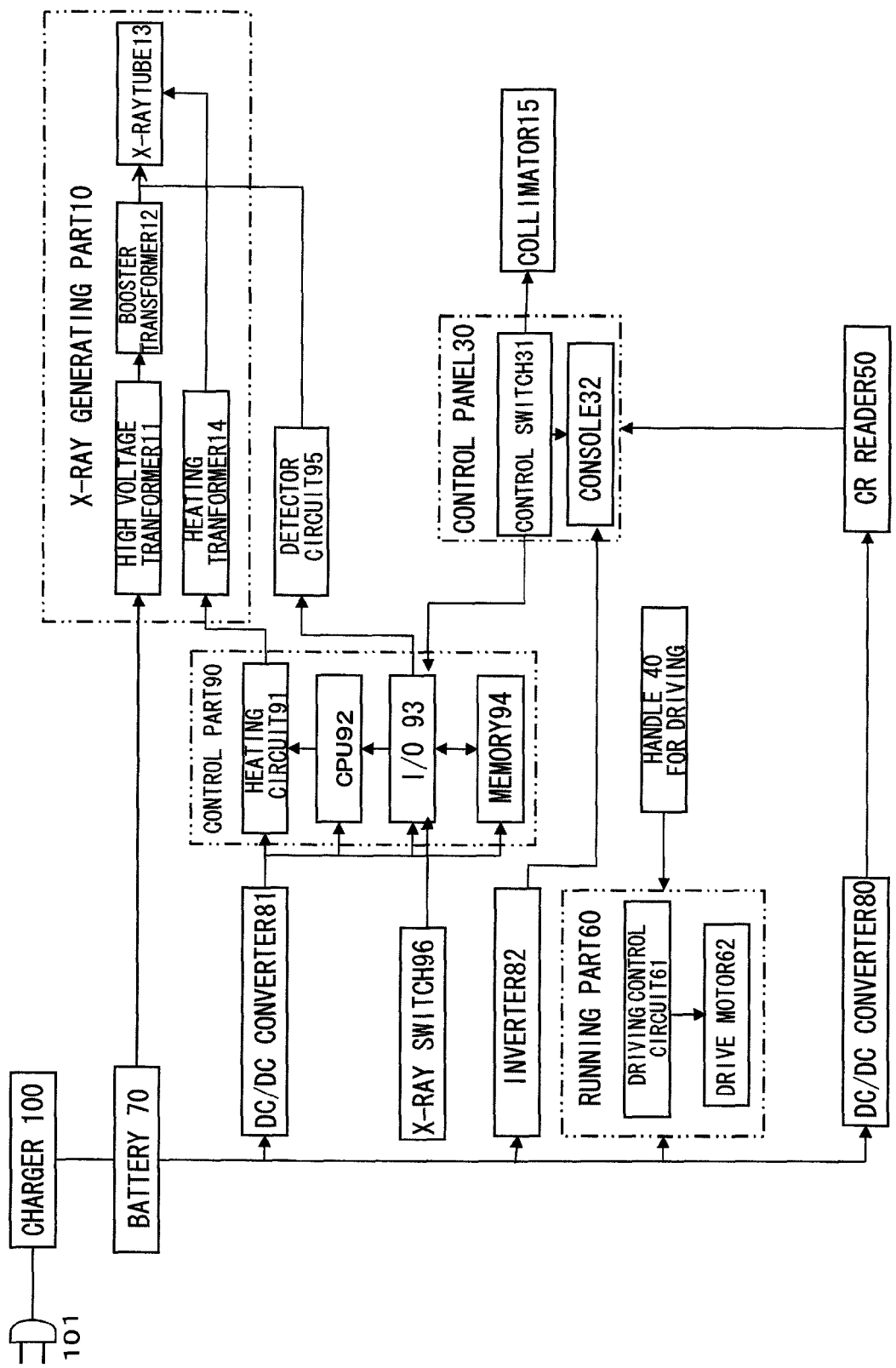
FIG. 2 is a functional block diagram of the mobile X-ray device according to the first embodiment.

Hereafter, with reference to FIG. 2, the internal configuration of the mobile X-ray device 1 will be explained. FIG. 2 is a functional block diagram of the mobile X-ray device according to the first embodiment.

The mobile X-ray device 1 is provided with the battery 70 and a charger 100 for charging the battery 70. The charger 100 is provided with an AC plug 101. If the AC plug 101 is connected to an AC electric socket on a site to which the device is moved, an alternating current acquired from the alternating current power supply is converted into a direct current, and used to charge the battery 70. By providing the charger 100 in the main body 2, the battery can be charged on a site to which the device is moved. Although the charger 100 is carried on the main body 2 in this embodiment, the battery 70 may be removably provided in the mobile X-ray device 1, and the charger 100 may be provided as a component independent from the mobile X-ray device 1. And the charger 100 may be disposed at a predetermined place, for example, a storage place of the mobile X-ray device 1, and the battery 70 removed from the main body 2 may be charged there. The mobile X-ray device 1 can be thereby made further smaller and lighter compared with the case where the charger 100 is carried on the mobile X-ray device 1.

The battery 70 supplies a direct current to a high voltage transformer 11 of the X-ray generating part 10, a direct current power source voltage conversion part (henceforth referred to as "DC/DC converter") 81 for control part 90, an inverter 82 for the control panel 30 (more precisely, a console 32 described later provided in the control panel 30), a driving control circuit 61 of the running part 60, and the DC/DC converter 80 for the CR reader 50.

The X-ray generating part 10 is provided with the high voltage transformer 11 for transforming voltage of the direct current supplied from the battery 70, a booster transformer 12 for further increasing the voltage of the high voltage current generated by the high voltage transformer 11, an X-ray tube 13 provided with a target (not shown in the drawing) and a filament (not shown in the drawing), and a heating transformer 14 for transforming heating current for the filament. When the high voltage current transformed by the booster transformer 12 is applied between the target and the filament, thermoelectrons emitted from the filament collide with the target, and X-ray tube 13 thereby generates X-ray (exposure).

The control part 90 is provided with a heating circuit 91 for controlling the heating transformer 14, a CPU (central processing unit) 92, an I/O 93 connected to an X-ray switch 96 and a control switch 31 for an operator to perform input operation, and a memory 94 for transmitting or receiving data to or from the I/O 93 and temporarily storing them. The I/O 93 is connected to a detector circuit 95. The detector circuit 95 is connected to the X-ray tube 13. When the X-ray switch 96 is turned on, the detector circuit 95 detects an exposure signal of X-ray through the I/O 93 and outputs an exposure signal to the X-ray tube 13, and X-ray is emitted from the X-ray tube 13.

The DC/DC converter 81 for the control part 90 transforms the direct current supplied from the battery 70 to a rated voltage suitable for supply to each constituent of the control part 90.

The control panel 30 is provided with a control switch 31 for controlling aperture of the collimator 15 or inputting other instructions for control, and the console 32 provided with an input device such as keyboard or touch panel, a display device for displaying an X-ray image read out by the CR reader 50, and a control device for controlling various operations in the console 32. The console 32 is equipped with an AC/DC converter inside, and driven with an alternating current power supply.

The main body 2 is provided with an inverter 82. The inverter 82 converts the direct current supplied from the battery 70 into an alternating current. The converted alternating current is supplied to the console 32.

The running part 60 is provided with the driving control circuit 61 and a drive motor 62 for motor drive of the wheel 63. Moreover, the handle 40 for driving is provided with a brake (not shown in the drawing) for an operator to apply braking during running of the mobile X-ray device 1. The driving control circuit 61 controls this brake and the drive motor 62. When an operator gives a braking operation, the driving control circuit 61 applies braking to the drive motor 62. If braking is canceled, the driving control circuit 61 drives the drive motor 62 to run the mobile X-ray device 1.

The main body 2 is provided with the CR reader 50. The CR reader 50 is provided with a loading port for inserting an imaging plate on the outer surface. Moreover, the main body 2 is provided with the DC/DC converter 80 for transforming the direct current of the battery 70 according to the rated voltage of the CR reader 50. The DC/DC converter 80 transforms the direct current of the battery 70 to the rated voltage of the CR reader 50. The transformed direct voltage is applied to the CR reader 50. When an imaging plate is inserted from the loading port, the CR reader 50 reads out X-ray image information from the imaging plate, and an X-ray image is displayed on the display device of the console 32. When the reading out of the X-ray image information is completed, the CR reader 50 erases the X-ray image information in the imaging plate.

Figure 3:
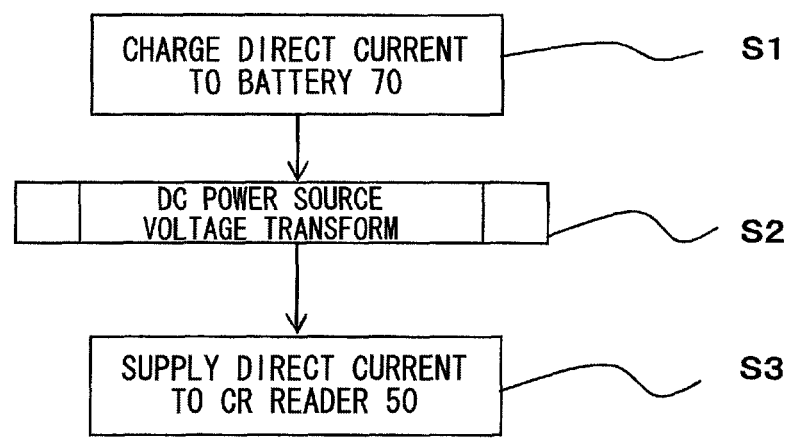
FIG. 3 is a flowchart showing flow of electric power supply in the mobile X-ray device according to the first embodiment.

Hereafter, flow of electric power supply in this embodiment will be explained with reference to FIG. 3. FIG. 3 is a flowchart showing flow of electric power supply in the mobile X-ray device 1 according to this embodiment.

In S1, the battery 70 is charged with a direct current (S1). This direct current is supplied to the DC/DC converter 80.

In S2, the DC/DC converter 80 transforms the direct current supplied from the battery 70 to the rated voltage of the CR reader 50 (S2).

In S3, the rated voltage transformed in S2 is applied to the CR reader 50 (S3).

In the mobile X-ray device 1 according to this embodiment, the direct voltage (direct current voltage) of the battery 70 is transformed, and the CR reader 50 is driven by a direct current power supply. Therefore, the inverter and the AC/DC converter in the CR reader become unnecessary. Therefore, comparing with the conventional configuration, that is, the case where a mobile X-ray device is constituted by providing an inverter for converting the direct current from the battery 70 into an alternating current and a CR reader driven by an alternating current power supply, the number of the components can be reduced, thus miniaturization and weight saving of the mobile X-ray device can be attained, and in addition, power efficiency can be improved.

Moreover, the power consumption of the console 32 is smaller than the power consumption of the CR reader 50, and therefore the inverter 82 for the console 32 is smaller and lighter than the inverter required for operating a conventional CR reader driven by an alternating current power supply. Therefore, if the inverter for the console is mounted instead of the inverter for the CR reader, miniaturization and weight saving of the mobile X-ray device 1 can be attained.

Figure 4:
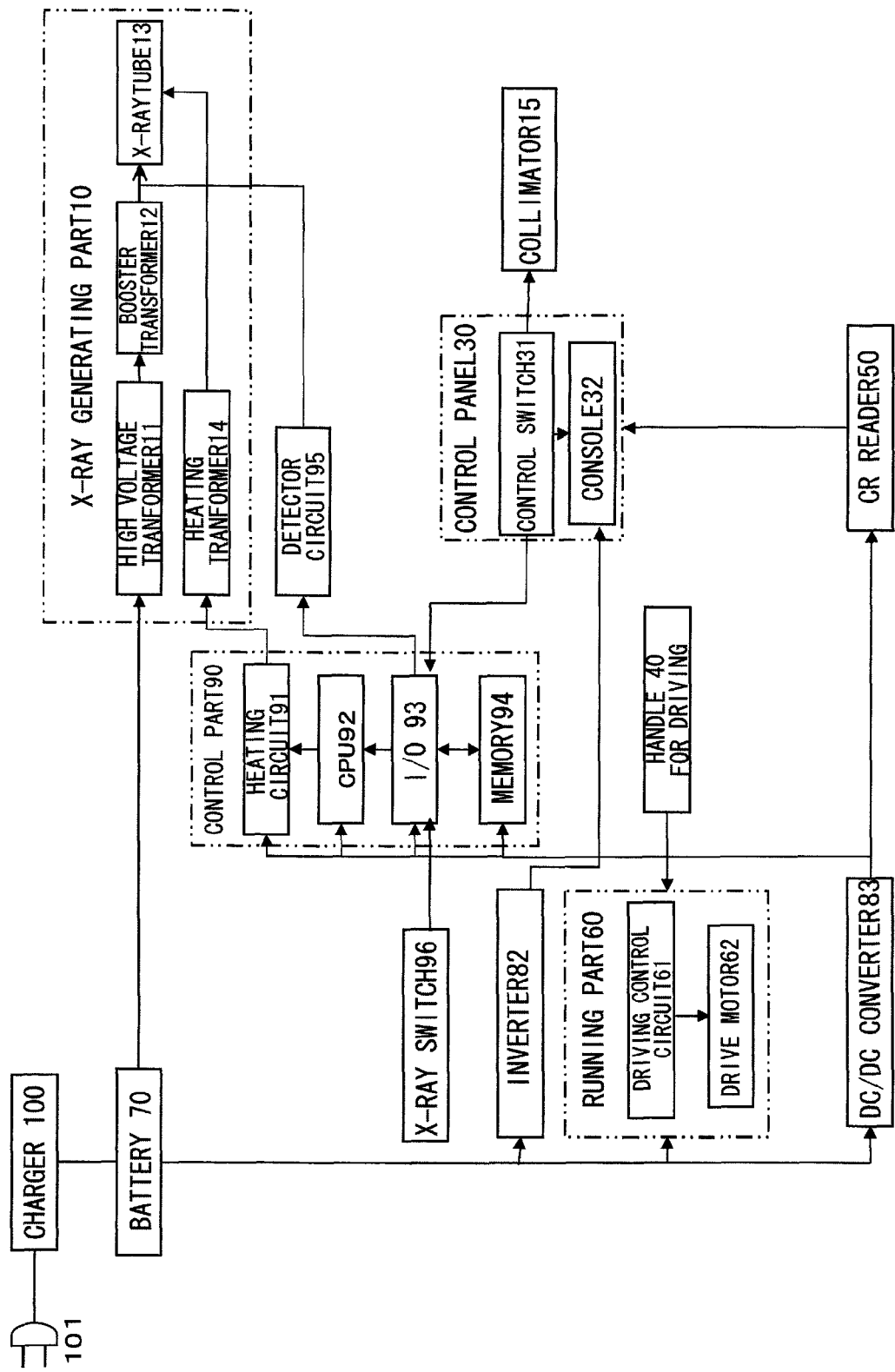
FIG. 4 is a functional block diagram of the mobile X-ray device according to the second embodiment.

In the first embodiment, the aforementioned battery 70 discharges a direct current corresponding to a rated voltage of the running part 60, a direct voltage from the battery 70 is applied to the running part 60, and for other constituents (devices), for example, the CR reader 50 and the control part 90, the DC/DC converters 80 and 81 for transformation to rated voltage of each are provided, respectively. In contrast, as shown in FIG. 4, the mobile X-ray device of the second embodiment is provided with a single DC/DC converter 83 instead of the DC/DC converters 80 and 81. And with this DC/DC converter 83, transformation to each of the rated voltages of the CR reader 50 and the control part 90 is attained. With such a configuration, the CR reader 50 and the control part 90 can share the DC/DC converter required for them, and further miniaturization and weight saving of the mobile X-ray device 1 can be attained.

Further, in the mobile X-ray device according to this embodiment, in order to use the conventionally existing console 32 driven by an alternating current power supply, the inverter 82 is provided, and direct current/alternating current conversion is performed with the inverter 82. However, the AC/DC converter in the console 32 may be removed, and a DC/DC converter for the console 32 may be provided, so that a direct current is supplied from the battery 70. Thereby, the inverter 82 and the AC/DC converter in the console 32 can be made unnecessary. Furthermore, the DC/DC converter for the console 32 may be used also as the DC/DC converter 83 of FIG. 4, and transformation for all the devices of the mobile X-ray device 1 may be attained with a single DC/DC converter. Thereby, further miniaturization and weight saving of the mobile X-ray device 1 can be attained.

EXPLANATIONS OF NUMERICAL NOTATIONS

1: Mobile X-ray device, 2: main body, 10: X-ray generating part, 15: collimator, 20: pole, 21: arm part, 30: control panel, 40: handle for driving, 50: image reader, 60: running part, 63: wheel, 70: battery, 80: DC/DC converter, 81: DC/DC converter, 82: inverter, 90: control part, 96: X-ray switch, 100: charger, 101: AC plug

The invention claimed is:

1. A mobile X-ray device comprising:
    a main body having an X-ray generating part, an image reader for reading X-ray image information from an imaging plate storing the X-ray image information, and a console equipped with an AC/DC converter inside;
    a running part for running the main body;
    a battery for storing direct current electrical energy to be supplied to the running part and discharging a direct current at a rated voltage of the running part;
    a first direct current power source voltage conversion part, located between the battery and the image reader, for transforming direct voltage of the battery to a rated voltage of the image reader; and
    an inverter, located between the battery and the console, for converting the direct current of the battery to an alternating current,
    wherein the rated voltage of the image reader, resulting from the direct voltage of the battery being transformed by the first direct current power source voltage conversion part, is applied to the image reader, and
    wherein the alternating current, resulting from the direct current of the battery being converted by the inverter, is applied to the console.

2. The mobile X-ray device according to claim 1, further comprising:
    a control part for controlling the mobile X-ray; and
    a second direct current power source voltage conversion part for transforming the direct voltage of the battery to a rated voltage of the control part,
    wherein the rated voltage of the control part, resulting from the direct voltage of the battery transformed by the second direct current power source voltage conversion part, is applied to the control part.

3. The mobile X-ray device according to claim 1, wherein the console is provided with a display device for displaying the image data read by the image reader, an input device for inputting instructions for operations, and a control device for controlling the display device and the input device.

* * * * *